United States Patent
Donato et al.

(10) Patent No.: US 6,923,993 B2
(45) Date of Patent: Aug. 2, 2005

(54) **PROCESS OF ISOLATING EXTRACT FROM THE *EUPHORBIA OBESA* PLANT AND METHODS FOR USING THE SAME**

(75) Inventors: Nicholas D. Donato, 1412 San Pablo Dr., San Marcos, CA (US) 92069; Nicholas J. Donato, 815 Sandpiper, Sugarland, TX (US) 77478; David C. Sample, Porter, TX (US); Margot Perez, Houston, TX (US); John S. McMurray, Houston, TX (US); Robert A Newman, Sugarland, TX (US)

(73) Assignees: Nicholas J. Donato, Sugarland, TX (US); Nicholas D. Donato, San Marcos, CA (US)

( * ) Notice: Subject to any disclaimer, the term of this patent is extended or adjusted under 35 U.S.C. 154(b) by 0 days.

(21) Appl. No.: 10/020,816

(22) Filed: Dec. 12, 2001

(65) Prior Publication Data

US 2003/0118677 A1 Jun. 26, 2003

(51) Int. Cl.⁷ .............................................. A61K 35/78
(52) U.S. Cl. ....................... 424/773; 424/725
(58) Field of Search .................. 424/725, 773

(56) References Cited

U.S. PATENT DOCUMENTS 6,432,452 B1 * 8/2002 Aylward

FOREIGN PATENT DOCUMENTS

| BR | 9701179 | * 12/1998 |
| WO | 9908994 | * 2/1999 |

OTHER PUBLICATIONS

Internet reference titled "*Euphorbia obesa* Hook. f." from website http:://www.plantzafrica.com, Feb. 2002, 4 pages.*
Vosa et al. Caryologia. 1994. vol. 44, No. 1, pp. 27–34, BIOSIS Abstract enclosed.*

* cited by examiner

Primary Examiner—Christopher R. Tate
(74) Attorney, Agent, or Firm—G. Peter Albert, Jr.; Foley & Lardner LLP

(57) ABSTRACT

The present invention is directed to a process of isolating an extract from a *Euphorbia obesa* (EO) plant by: preparing a sample of said plant comprising removal of the latex material; dissolving said sample with first solvent to form a solution; separating said solution into a liquid and a pulp fraction; and purifying said pulp fraction. The isolated EO extract induces apoptosis and inhibits growth of a cancerous cell. Thus, the present invention is also directed to a method for inducing apoptosis and growth inhibition of a cancerous cell by contacting the cell with an effective amount of the EO extract by the process of the invention. Preferably, the extract is administered both to the tumor directly and intravenously. The preferred lines of cancerous cells are melanoma, non-small cell lung cancer, prostate cancer, breast carcinoma, ovarian cancer, lymphoma and leukemia cells.

57 Claims, 10 Drawing Sheets

FIG. 1

| Tumor Type | Cell line | Response | Assay |
|---|---|---|---|
| Melanoma | A375P | +++ | a,b |
| | A375M | ++ | a |
| | Hs294T | + | a |
| | DX-3 | NR | a |
| | SKMel-28 | NR | a |
| | Mel-21 | NR | a |
| | M-21 | + | a |
| | AAB-1 | ++ | a |
| | AAB-2 | + | a |
| Breast | BT-20 | NR | a |
| | MCF-7 | + | a |
| | MCF-7/TNFR | ++ | a |
| | SKBr-3 | + | a |
| Prostate | Du-145 | NR | a |
| | PC-3 | + | a |
| | LnCaP | +++ | a,b |
| Ovarian | SKOV-3 | NR | a |
| | NIH-OVCAR-3 | NR | a |
| | HEY | ++ | a,b |
| Cervical | ME-180 | NR | a |
| Vulvular | A431 | NR | a |
| Non-small cell lung | H322 | + | a,b |
| | H522 | ++ | a,b |
| Colon | Ls174T | NR | a |
| Lymphoma | Raji | NR | b |
| | Jurkat | + | b |
| | U937 | +++ | b |
| Leukemia | K562 | +++ | b |
| | Molt-4 | ++ | b |
| | HSB-2 | NR | b |
| | THP-1 | + | b |
| Normal Skin Fibroblasts | CRL-2103 | NR | a |

FIG. 2
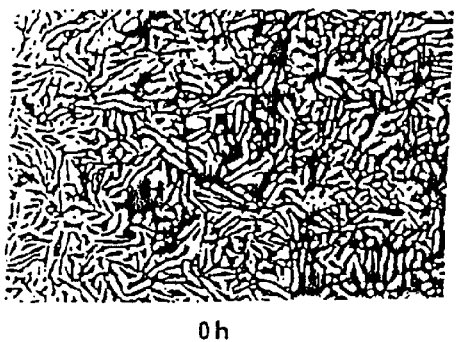
0 h
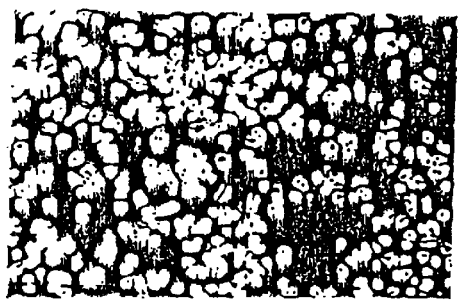
12 h
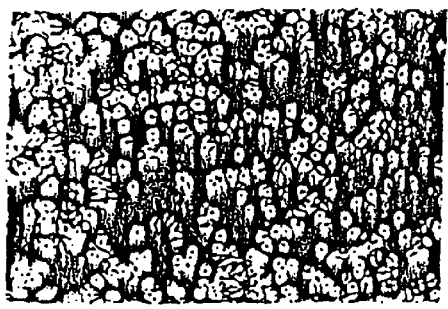
4 h
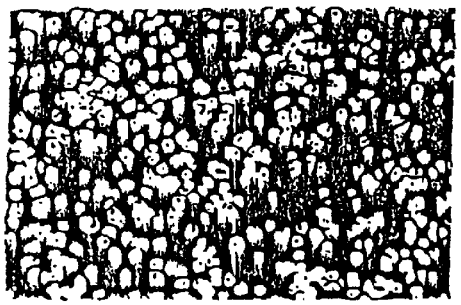
24 h
8 h
DMSO FIG. 3
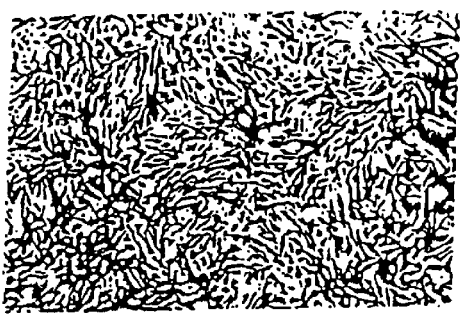
0 h
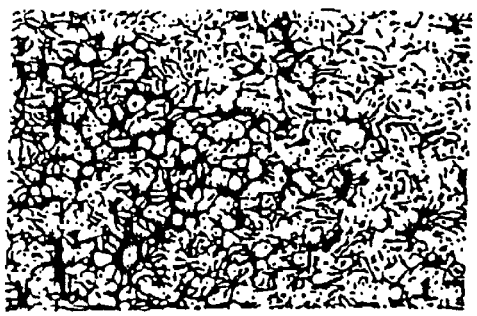
12 h
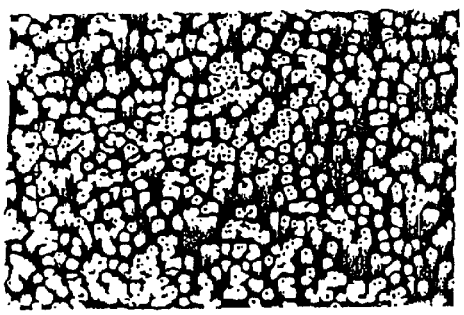
4 h
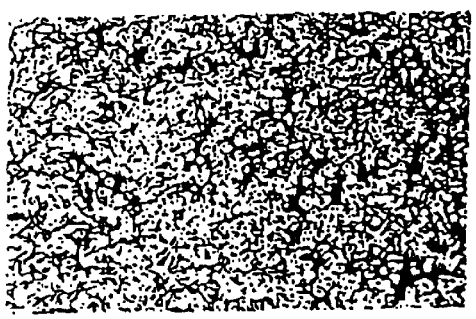
24 h
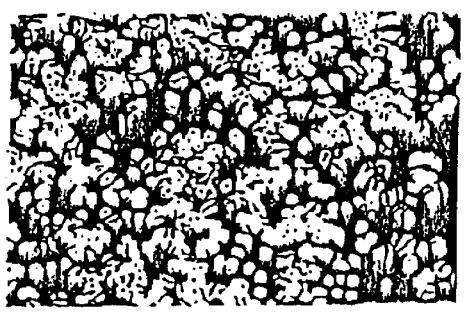
8 h
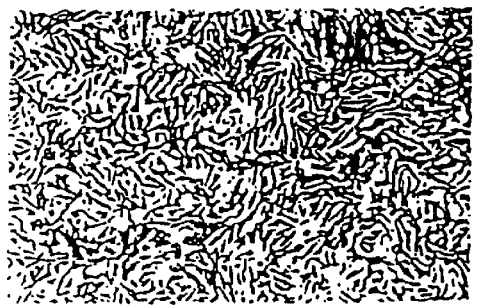
DMSO FIG. 4
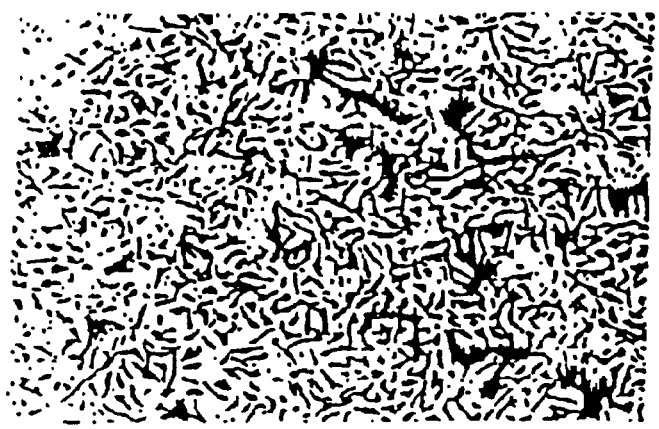
0 h
4 h
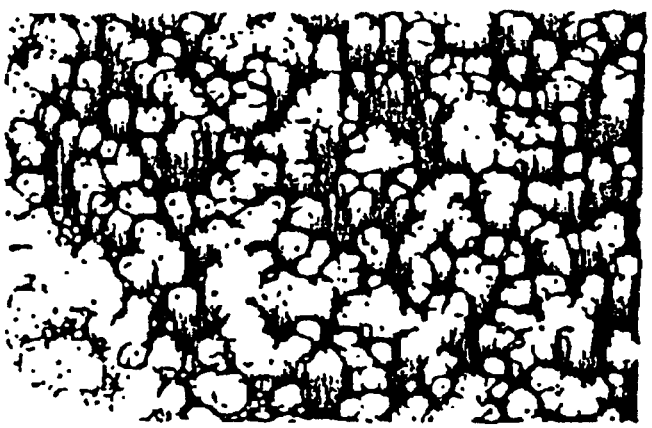
48 h FIG. 5
DMSO | Extract
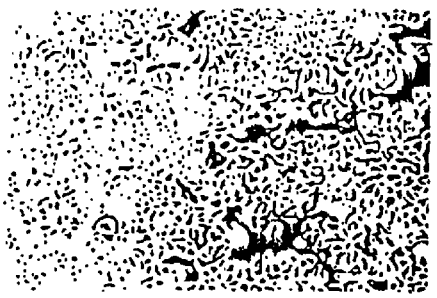 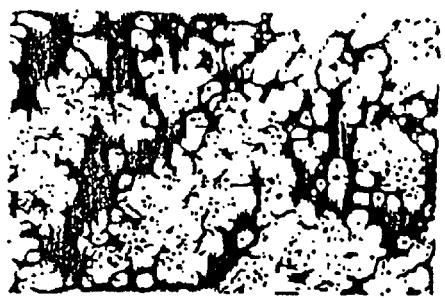
H322
 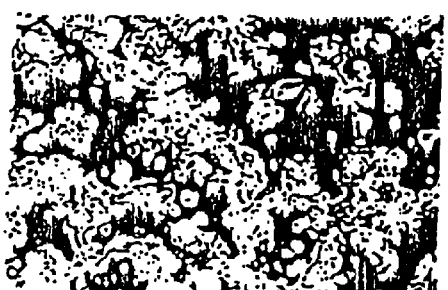
H522
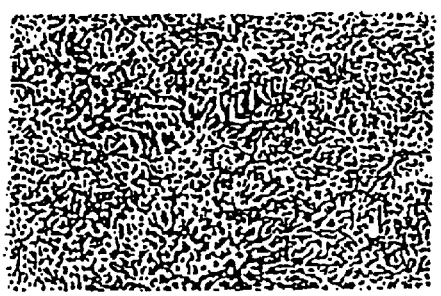 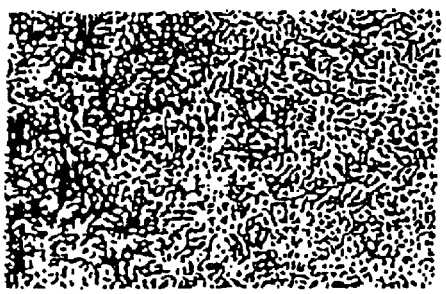
A431
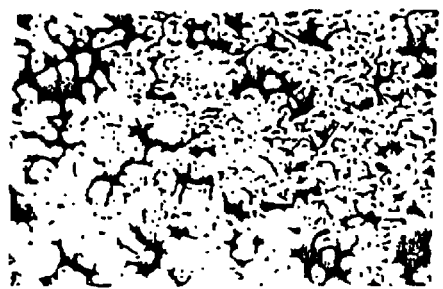 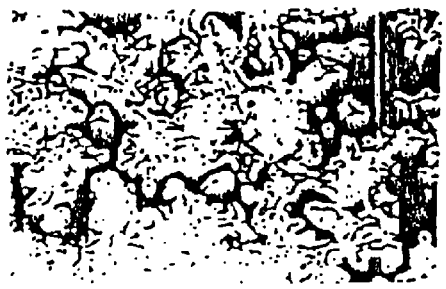
LnCaP

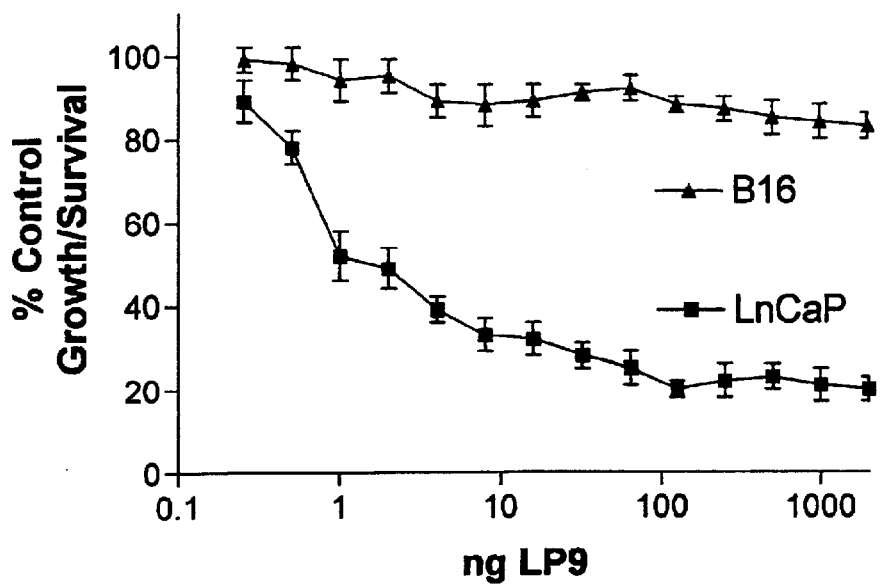
FIG. 8(a)
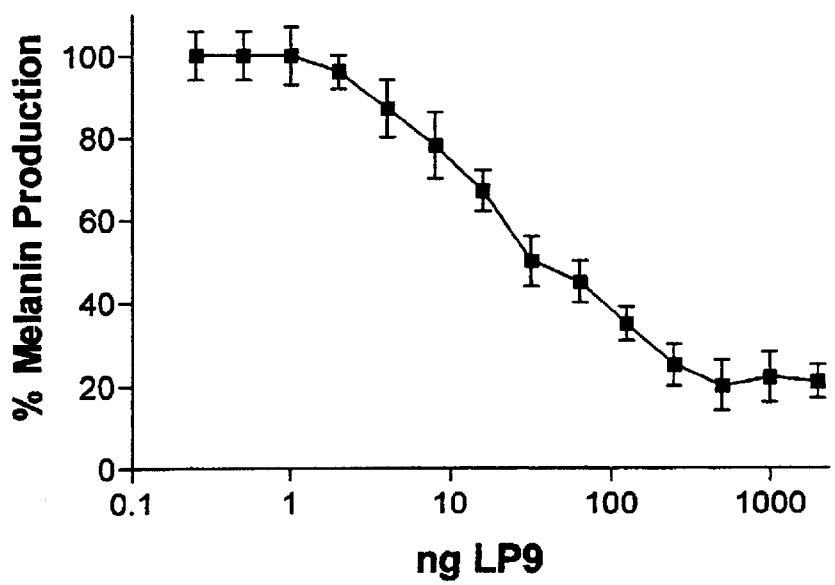
FIG. 8(b)
FIG. 8

FIG. 9

| Treatment | Route | # Animals | # With Tumor | % Tumor Positive |
|---|---|---|---|---|
| Control (PEG300-DMSO) | Intratumoral + Intraperitoneal | 10 | 9 | 90 % |
| LP9 (1 mg) | Intratumoral + Intravenous | 8 | 7 | 87.5 % |
| LP9 (1 mg) | Intratumoral + Intraperitoneal | 9 | 3 | 33 % |

PROCESS OF ISOLATING EXTRACT FROM THE *EUPHORBIA OBESA* PLANT AND METHODS FOR USING THE SAME

TECHNICAL FIELD OF THE INVENTION

This invention generally relates to compounds for treating cancer that are derived from plants and, in particular, the isolation and use of an extract from a *Euphorbia obesa* plant having anti-tumor effects on a variety of cancerous cell.

BACKGROUND

Plants and marine organisms provide a rich source of compounds that have been investigated and exploited for a variety of medicinal and biological applications. The Euphorbiaceae family is one of the largest families of plants with about 300 genera and 7,500 species, mostly monoecious herbs, shrubs and trees, sometimes succulent and cactus-like, that are further frequently characterized by a milky sap or latex material. Members of the Euphorbiaceae family have been investigated as providing potential treatments for cancers, tumors and warts. Active components found in members of this plant family may be common to several genera or species of the family or may be limited to a particular genus or species.

Certain Euphorbiaceae species have been shown to synthesize phorbol ester and diterpene diester compounds having therapeutic effects on certain cancers. For instance, the isolation and characterization of antileukemic properties from *Euphorbia esula* L and *Croton tiglium* L. have been reported. S. M. Kupchan et al., Science 191: 571–572 (1976). The fractionation of an active extract led to the characterization of the antileukemic component from *Euphorbia esula* L as a diterpene diester. Fractionation of croton oil led to the characterization of the active component known as a phorbol diester, phorbol 12-tiglate 13-decanoate.

One of the most investigated phorbol ester derived from certain members of the Euphorbiaceae family is TPA, 12-O-tetradecanoyl-13-phorbol acetate. Although TPA is primarily recognized as a tumor promoter when topically applied to the skin of mice, the compound was also found to stimulate differentiation and inhibit DNA synthesis of HL-60 human promyelocytic leukemia cells in vitro. The effect of this compound when administered to human patients with myeloid malignancies was also examined. Intravenous dosages of 1 mg of TPA was shown to have pharmacological activity for the treatment of myelocytic leukemia in patients refractory to cytosine arabinoside, retinoic acid and other antileukemic drugs. Han et al. Proc. Nat'l Acad. Sci. 95; 5357–5361 (1998). Likewise, the intravenous administration of TPA in human patients having low white blood cell (WBC) counts due to prior treatments of solid tumors with a cytotoxic chemotherapuetic agent, caused an increase in WBC count and neutrophilia in the blood. Han et al. Proc. Nat'l Acad. Sci. 95; 5362–5365 (1998).

However, the administration of TPA, even at relatively small doses of 0.5 to 1 mg appeared to have toxic effects in vivo. Moreover, the therapeutic effects appear to be limited to a particular cell type or particular mode of administration. Further, no distinction was made in the references to whether TPA, and any other active component derived from plants from the Euphorbiaceae family, was obtained from the outer cortex or latex material of the plant.

The phorbol esters derived from other Euphorbiaceae species that are examined in these references have different physical and chemical properties as compared to the extract of the present invention, which is derived from the *Euphorbia obesa* (hereinafter, "EO") species. For instance, when compared to TPA by thin layer chromatography (TLC) analysis, the EO extract of the present invention has different mobilities. In addition, the absorption max and visible color of the EO extract and TPA are distinct. EO is a succulent, thornless, cactus-like plant that grows in temperate climates and is typically used in gardens for their ornamental value. Due to its ribbing or stitch-like ridges, the plant is commonly referred to as "the baseball plant." No biological or medicinal properties have been identified from this particular species. Thus, there is a need to isolate and evaluate novel compounds having anti-tumor activity from the EO species of the Euphorbiaceae family.

SUMMARY OF THE INVENTION

The present invention relates to a method for isolating an extract from a EO plant that induces apoptosis and inhibits growth of a cancerous cell by: removing the latex material from the plant; dissolving pieces of the plant into a first solvent, preferably a mixture of methanol and chloroform, to form a solution; separating said solution into a liquid and a pulp fraction; and purifying the pulp fraction. The preferred method involves using the bulb portion of the plant without the roots, outer cortex and latex. Preferably, the process further comprises exchanging the first solvent for a second solvent, such as DMSO, methanol or a mixture of hexane and chloroform. Preferably, the purifying step comprises multiple subparts that result in a purified extract consisting of primarily a single compound. The preferred subparts of the purification process are: silica column chromatography, DEAE-Sephacel anion exchange chromatography, reverse phase high performance liquid chromatography (HPLC) and preparative thin-layer chromatography. Preferably, the bioactivity of the pulp fraction is detected by incubating the pulp fraction with LnCaP prostate cancer cells, wherein apoptosis occurs in >50% of the incubated cells.

The present invention is also directed to a method for inducing apoptosis and growth of a cancerous cell by isolating an extract from an EO plant as described above and contacting said cancerous cell with an effective amount of the extract. Preferably, the extract used in this method is a purified extract comprising a single compound; alternatively, a partially-purified extract could be used that comprises a plurality of compounds. The extract may contact the cancerous cell in vitro or in vivo; where the extract is administered in vivo, the preferred mode of administration is intratumor and intraperitoneal injections. The cancerous cells most responsive to the EO extract appear to be lines of melanoma, non-small cell lung cancer, prostate cancer, ovarian cancer, breast cancer, lymphoma and leukemia cells.

BRIEF DESCRIPTION OF THE DRAWINGS

FIG. 1 depicts a table showing the effect of EO extract in inducing cytotoxicity in a variety of cell lines. In the column labelled "response", the designation "+++" means that the extract induced cytotoxicity in >75% of the sample cells; "++" means that the extract induced cytotoxicity in >50% of the same cells; "+" means >25% of the cells were effected; and "NR" means the sample was non-responsive to the extract. In the column labelled "assay", "a" stands for crystal violet staining and "b" stands for Promega proliferation assay. The results shown in the table result from incubation with 50 μg/ml of partially-purified EO extract for 72 hours and represent the average of 4 determinations.

FIG. 2 comprises photographs of EO extract-induced morphological changes in A375P melanoma cells after incubation for 0 hours, 4 hours, 8 hours 12 hours and 24 hours, and a photograph of control cells treated with DMSO only after 24 hours of incubation.

FIG. 3 comprises photographs of EO extract-induced morphological changes in Hs294T melanoma cells after incubation for 0 hours, 4 hours, 8 hours 12 hours and 24 hours, and a photograph of control cells treated with DMSO only after 24 hours of incubation.

FIG. 4 comprises photographs of EO extract-induced morphological changes in Hey ovarian cancer cells after incubation for 0 hours, 4 hours and 48 hours.

FIG. 5 comprises photographs of EO extract-induced morphological changes in H322 and H522 non-small cell lung cancer cells, vulvular A431 cells, and LnCaP prostate cancer cells, after incubation for 24 hours, as compared to control cells treated with DMSO only, also after 24 hours of incubation. As can be seen, morphological changes occurred in the non-small lung cancer cells and the prostate cancer cells, but not the vulvular cells.

FIG. 8 comprises two charts. FIG. 8a shows the effect of the purified extract on the growth and survival of LnCaP and B16 cells after 48 hours of incubation, as determined by crystal violated staining. Each data point represents the average S.E.M. of 4 determinations. Similar results were obtained with other proliferative/survival assays. FIG. 8b shows the effect of purified extract on B16 cells in inducing melanin production. The results suggest a biological effect of extract on melanin production that parallels that detected by the anti-tumor effects of the extract on LnCaP cells.

FIG. 9 comprises a table that shows the results of BDF-1 mice injected with $5 \times 10^5$ B16 melanoma cells and then treated with LP9 or control via intratumoral; and intraperitoneal injections, or via intratumoral and intravenous injections. The animals received additional treatment after 7 days and 14 days, and tumor presence was evaluated on the $20^{th}$ day. Six of nine animals treated with the extract by intraperitoneal and tumor site injections had no visible signs of tumor, whereas a majority of animals in the control and i.v./i.t group had large tumor burden, i.e., greater than 1.5 cm in diameter.

DETAILED DESCRIPTION OF INVENTION

Figure 6:
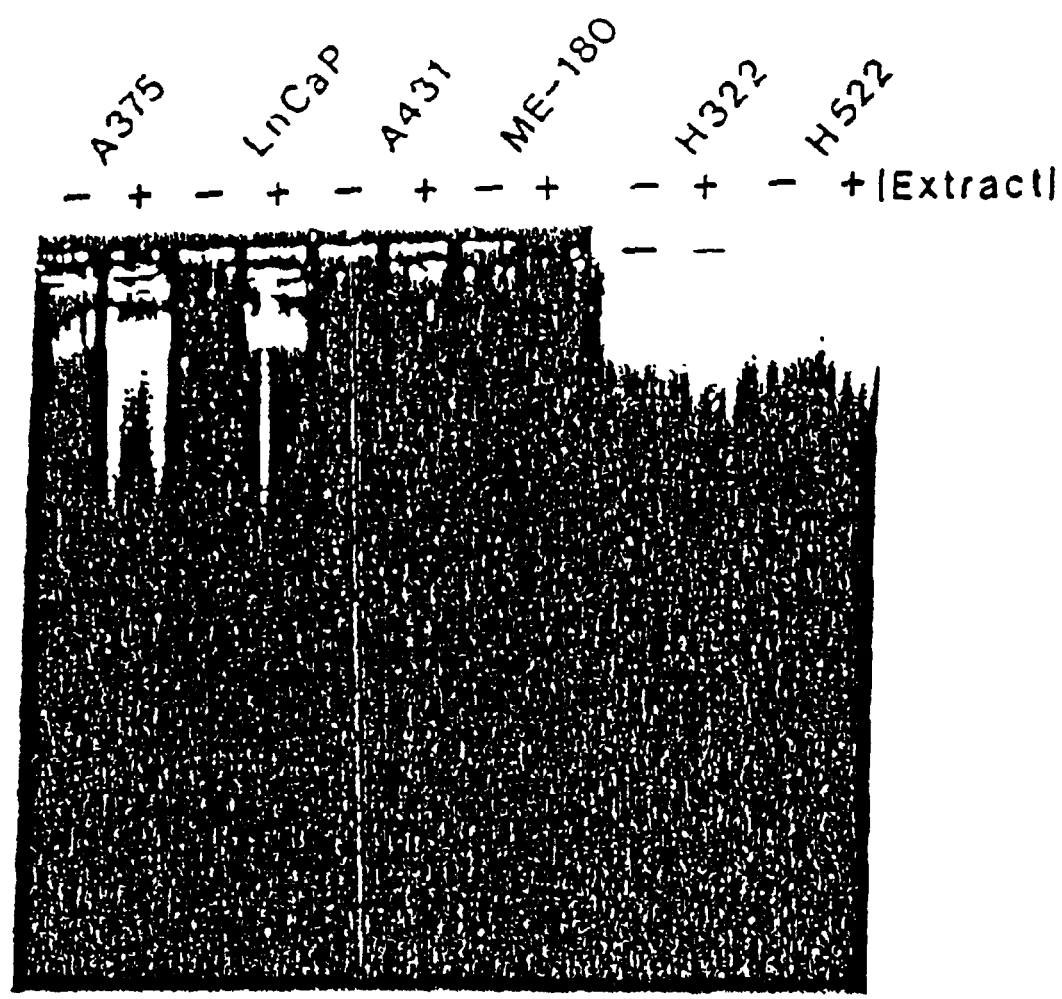
FIG. 6 shows the effect of EO extract on DNA fragmentation in responsive and unresponsive tumor cells. DNA extracted from 6 cell lines were treated with 50 $\mu$g/ml of plant extract (+) or DMSO (-) for 24 hours and were analyzed for evidence of DNA degradation into laddered fragments by agarose gel electrophoresis. Equal amounts of DNA were loaded into wells representing control (with DMSO) and treated cells. Evidence of DNA laddering can be seen in A375 melanoma and LnCaP prostate cell extracts whereas extract resistant cells, such as A431 and ME-180, demonstrated no changes in DNA integrity.

The present invention is directed to the isolation of an extract from an *Euphorbia obesa* (hereinafter "EO") plant that induces cytotoxicity of cancerous cells and inhibits their growth. Preferably, the extract is derived from the bulb of the plant, removing and therefore excluding any effect of the roots, outer cortex or latex material of the plant. The latex material separates the outer cortex and inner bulb of the plant.

The first step of the method of isolating a bioactive extract from an EO plant comprises preparing a sample of the plant wherein the plant is rinsed in cold water and the outer cortex, latex material and roots have been removed, leaving primarily the bulb portion of the plant. Preferably, a smaller plant that weighs less than 100 g is used.

Next, the sample is dissolved with a first solvent to form a solution. Preferably, the first solvent comprises chloroform and methanol. This step may occur by cutting the sample into small pieces, grinding it to a slurry with a mortar and pistle, and dissolving the slurry in approximately 1.0 L to approximately 2.5 L of Chl:MeOH. Alternatively, this step may occur by cutting the sample into small pieces and blending these pieces in a blender for about 2 minutes with approximately 3 L of Chl:MeOH.

Next, the solution is processed so that it separates into an aqueous upper liquid and a less aqueous, pulp-like, lower fraction. This separation may occur by known techniques, such as centrifugation. Alternatively, this separation may occur by filtering the sample through a frittering glass funnel under a vacuum, re-blending the filtered liquid with Chl:MeOH and water in a separatory funnel, and inverting the funnel several times. The lower pulp fraction is retained, while the upper liquid is set aside or discarded.

Next, the pulp fraction is further processed so that the first solvent is exchanged for a second solvent. This step is performed by evaporating the pulp fraction into a concentrate and dissolving this newly formed concentrate into a second solvent, which preferably comprises either dimethylsulfoxide (DMSO), methanol or hexane:chloroform, in a proportion of 95:5. Evaporation may occur by vacuum evaporation, such as with a Speed Vac or a Rotovap vacuum concentrator. At this point, a precipitate may form, which should be removed from the pulp fraction.

Next, the solution is purified to isolate a purified or at least partially purified extract that demonstrates bioactivity. The "bioactivity" of an extract may be determined by several assays. Preferably, a bioactive extract induces apoptosis of more than 50% of LnCaP prostate cancer cells upon incubation. Although other cell lines were used for testing apoptosis or growth inhibition with the extract, such as incubation with the A375 melanoma cell line, the LnCaP cell line is preferred because it provides a rapidly detectable and quantitative cellular response. That is, bioactivity is determined by incubating LnCaP prostate cancer cells with the pulp extracted fraction and measuring any cellular response. Typically, within 2 to 6 hours of incubation, a bioactive extract will cause the cells to appear more flattened and demonstrate cellular adhesion. After 24 hours, if the extract is bioactive, the clustered cells will appear apoptotic, as detected by changes in PARP cleavage, caspase activation and quantification by known means such as MTT or crystal violate assays.

Preferably, the purification step is comprised of a series of subparts. Although the preferred extract is a "purified" extract derived after all of the following subparts are performed, the extract derived after each subpart may also have useful bioactive properties. For instance, a "crude" extract derived after silica column chromatography only has been shown to induce cytotoxicity in several cell lines, as described in more detail below. Moreover, a "partially purified" extract derived after DEAE-Sephacel chromatography was found to induce apoptosis and inhibit growth of certain cancerous cells.

The first subpart of the purification step preferably comprises silica column chromatography, wherein the pulp fraction is applied to a silica gel column, which may be equilibrated with known media, such as chloroform or hexane:ethyl acetate (80:20). The pulp fraction is applied to the silica gel column with step increases in the appropriate solvent, such as chloroform (Chl):methanol (MeOH) or hexane:ethyl acetate. Preferably, the silica gel column is equilibrated with chloroform and the pulp fraction is applied with 5% step increases in Chl:MeOH, starting at 95% Chl:5% MeOH. Most preferably, the fractions eluted at 90% Chl:10% MeOH are pooled, concentrated and stored for further use, as these fractions were found to be the most bioactive according to the bioactivity assay described above. Alternatively, the silica gel column may be equilibrated with ethyl acetate:hexane, wherein the most bioactive fractions are eluted at 20% ethyl acetate:80% hexane, and 30% ethyl acetate:70% hexane.

The next subpart of the purification process preferably comprises DEAE anion exchange chromatography. The active fractions from silica column chromatography are diluted and mixed with DEAE-Sephacel that has been equilibrated in chloroform. The slurry of EO extract and DEAE-Sephacel is stirred and poured into a funnel under suction. The packed material is sequentially washed with 100% Chl, 90% Chl:10% MeOH; 80% Chl:20% MeOH; 70% Chl:30% MeOH, etc. Collected fractions are again analyzed for bioactivity as described above, and the most active fractions are found to elute at 70% Chl:30% MeOH. Thus, these fractions are also pooled, concentrated and stored for future use.

Preferably, the next subpart involves HPLC (high performance liquid chromatography). That is, active fractions from the DEAE-Sephacel fractionation are resolved by reverse phase HPLC on a Vyadac C18 column. The column is equilibrated with double distilled water, and aliquots of the pulp fraction are applied with increasing amounts of MeOH solvent in a linear gradient. Again, the fractions are collected and analyzed for bioactivity, and the most bioactive fractions are detected at 95% MeOH:5% water, which are again pooled, concentrated and stored.

The final subpart involves thin-layer chromatography (TLC). That is, the HPLC purified extract is applied to the bottom of a silica gel plate, and the plate is placed in a chromatography tank containing ethyl acetate and developed until the solvent front reaches the top of the plate. Fractions were collected from the plate, preferably with 100% MeOH, centrifuged and concentrated. Bioactivity was detected in samples taken at an Rf value of approximately 0.75 to 0.80. These bioactive samples were concentrated and reapplied to a similar TLC plate but developed in a solvent consisting of 95% Chl:5% MeOH containing 0.25% aqueous ammonia. Bioactivity in this solvent system was detected at an Rf value of approximately 0.5 to 0.6.

The purified plant extract may then be analyzed using well known techniques, such as thin-layer chromatography, and detected by charring formaldehyde-sulfuric acid sprayed plates. A single spot is detected in the purified final product. The partially purified extract derived after the step of DEAE-Sephacel chromatography has 6–7 detectable spots. It is not clear whether contaminants in the DEAE Sephacel fraction effect the bioactivity of partially-purified extract in vivo, but the purified extract is nonetheless preferred.

The purified extract derived by the process described above has been found to be particularly effective with specific mammalian cell lines—i.e., melanoma cells, non-small lung cells, prostate cancer cells, breast carcinoma cells, ovarian cancer cells, lymphoma cells and leukemia cells. Preferably, the most responsive melanoma cells are of the following types: Hs294T, A375P, A375M, M-21, AAB-1, AAB-2 and B-16. The preferred non-small lung cells are H322 and H522 cells, while the preferred prostate cancer cells are LnCaP and PC-3 cells. The most responsive breast carcinoma cells are of the following types: MCF-7, MCF-7/TNFR, SKBr-3; the most responsive ovarian cancer cells are of the Hey type; of the lymphoma cells, Jurkat and U937 cells are most responsive; and of the leukemia cells, K562, MOLT-4 and THP-9 are most responsive.

Also contemplated by the present invention is a method for inducing cytotoxicity, growth inhibition and, preferably, apoptosis, of a cancerous cell comprising isolating an EO extract as described above and contacting said extract with said cancerous cell.

In vitro studies, described in more detail below in Example 2, show that a single dose of the "crude" extract contacting A375 and Hs294T melanoma cells was active in inducing early morphological changes and cytotoxicity. These early changes persist in A375 cells for more than 24 hours, but some recovery or partial reversal of this effect is seen in Hs294T cells. The effects of extract on cell survival and morphology of other normal and tumor cell lines were also examined. The results are shown in FIG. 1.

In vitro studies of the purified and partially-purified extract also showed that the purified LP9 compound demonstrated some biological activity on human prostate cancer LnCaP cells and murine melanoma B16 cells, as described in more detail below in Example 4.

In vivo studies examined the effect of the purified and partially-purified extract on BDF-1 mice bearing subcutaneous tumors through inoculation with B16 melanoma cells. The extract was administered in a total dosage no less than 0.5 mg, and preferably approximating 0.5 mg, via three modes: (1) injections directly to the tumor (hereinafter "intra-tumor" or i.t.), and intravenously (i.v.); (2) i.t. injections and intraperitoneal (i.p.) injections; and (3) i.p. injection only. The second route of administration, i.t. and i.p., is preferred as it resulted in the greatest anti-tumor effect. This and other in vivo studies are described in more detail below, in Example 4.

These results also indicate that the EO extract is distinct from phorbol esters that have been previously reported in the literature. First, as mentioned above, the TLC migration of phorbol ester in the ethyl acetate:hexane solvent system bears no similarity to the migration of the purified and partially-purified plant extracts. Secondly, the EO extract induced apoptosis in A375 melanoma cells irreversibly following incubation with the extract for 4 hours, whereas the effects of phorbol esters on melanoma cell growth inhibition has been shown to be reversible. Finally, the growth of SK-Mel-28 cells has been inhibited by phorbol esters, but its growth was unaltered by incubation with plant extract.

EXAMPLE 1

Preparation "Crude" Extract

Ten plants, both male and female of the species, weighing between 50–250 g were used. After extensive washing of these plants in distilled water, their roots were cut away and discarded. Moreover, the outer cortex and latex fraction were removed. The plant materials were weighed, cut into small pieces, and ground to a slurry with a mortar and pestle. The plant samples were homogenized in 1.125 L to 2.25 L of methanol and chloroform, in a proportion of 1:2. The samples were centrifuged at 1000 g for 20 minutes, and an upper aqueous layer and lower organic layer were formed. The lower layer demonstrated anti-melanoma activity within 72 hours after incubation with A375 human melanoma cells. The methanol/chloroform solvent of the lower layer was then removed by Rotovap evaporation, and the viscous concentrate was resuspended in approximately 8 ml. of methanol and stored in an area protected from light at 4 degrees C.

To begin the purification process, the methanol solvent was exchanged for hexane:chloroform (95:5) by speed Vac evaporating the methanol fraction and resuspending the residue by sonication in hexane:chloroform. This solution was then applied to a silica gel column (1.2×10.5 cm) equilibrated in 80% hexane and 20% ethyl acetate. Thirty ml aliquots of solvent containing 10% incremental adjustments in hexane:ethyl acetate content—i.e., 80:20, 70:30, 60:40, etc.—were applied to the column and 10 ml. fractions were collected. After 100% ethyl acetate application, the column was eluted with methanol and the eluant was collected for a total of 31 column fractions.

To measure bioactivity, a 500 ul aliquot from each fraction was speed vac evaporated to dryness and the residue was resuspended in 25 ul of DMSO and stored at 4 degrees C. overnight. Each fraction was then mixed with 1½ ml of normal growth media, which were then vortexed, filter-sterilized and incubated with A375 melanoma cells pre-plated at a density of $8 \times 10^3$ cells/well in a 96-well plate 24 hours prior to the addition of column fractions. The most bioactive fractions, as determined by the factors described below, were fractions 3 and 6, which were eluted with 20:80 and 30:70 ethyl acetate:hexane respectively.

To determine the homogeneity of each fraction, a 50 ul aliquot of each fraction was resolved on TLC plates in 80% ethyl acetate, 20% hexane, sprayed with a methanol/sulfuric acid solution (4ml concentrated in H2SO4 in 100 ml methanol) and charred on a hot plate until spots were visible.

EXAMPLE 2

Effect of "Crude" Extract on Cell Lines

All cells examined were grown to 80–90% confluence in minimal essential media containing 10% fetal bovine serum and 50 ug/ml gentamycin. Monolayer cultures were trypsinized and reseeded in 96-well culture plates (0.5–1.5× $10^4$ cells/well) or 60 mm culture dishes (0.5–1.0×$10^6$ cells/dish) to examine the "bioactivity" of the extract—that is, cellular morphological changes, cellular growth inhibition, cytotoxicity and apoptosis induced following incubation with extract.

The cells were incubated for 4–72 hours at 37 degrees C. with extract solubilized in DMSO and diluted into media at a concentration of no greater than 50 ug solids/ml of media and a final DMSO concentration of 1%. Control cells received DMSO alone.

"Bioactivity" is determined by a number of factors. First, survival of the cells after incubation, which reflects the cytotoxicity of the extract, is assessed by procedures well known in the art, such as crystal violet staining or Promega proliferation assay. Secondly, morphological changes in the cells, such as cytoplasmic shrinkage, collapse of the plasma membrane and elongation of cellular extensions of the cells, were examined microscopically. Thirdly, non-adherent cell growth, which reflects the anti-proliferative effects of the extract, were analyzed by Cell Titer 96 Aqueous Non-Radioactive Cell Proliferation Assay available from Promega (Madison, Wis.). All assays estimating changes in cell growth were performed in quadruplicate and the results were reported as the average of 4 determinations with no more than 5% variance. Relative anti-proliferative effects were calculated using the following known formula:

$$\% \text{ Inhibition} = 100 \times \frac{\text{absorbance of treated cells-blank}}{\text{absorbance of control cells blank}}$$

Finally, bioactivity was determined by evidence of apoptosis, a cell death process characterized by chromatin fragmentation. The appearance of DNA "ladders" in cells committed to death is a known indication of chromatin fragmentation and, thus, apoptosis. To determine the role of apoptosis in cellular sensitivity to plant extract, cells incubated with the extract were examined for evidence of these DNA ladders. Following the release of adherent cells from the culture dish with a cell scraper, detached and released cells were collected by centrifugation (500×g, 4 degrees C., 2 min.) The cell pellet was washed once with 1 ml PBS and repelleted at 1500×g, 1 min. 4 degrees C. The final pellet was thoroughly resuspended in 50 ul of PBS and lysed by vortexing during the addition of 50 ul of 2× lysis buffer consisting of 40 mM Tris-HCL, pH 7.4, 80 $\mu$M EDTA and 1.6% sarcosyl. The lysate was incubated on ice for 10 minutes and 120 ug of protease K was added per 100 ul of lysate. The lysate was mixed and incubated at 50 degrees C. for 3 hours, transferred to 4 degrees C. and the incubation was continued for an additional 18 hours. Ribonuclease A was added to a final concentration of 10 ug/ml and incubation was continued at 50 degrees C. for 3–18 hours. DNA content in each lysate was estimated spectrophotometrically and equal quantities of DNA (~5–10 ug) were subjected to electrophoresis on 1.5% agarose gels, equilibrated in TAE buffer containing 0.5 ug/ml ethidium bromide, at 50V for 1.4 hours. After resolution of the DNA fragments, gels were placed on a UV transilluminator and photographed.

A single dose of extract induced early morphological changes and cytotoxicity in the human melanoma cell lines examined (A375 and Hs294T). Cytoplasmic shrinkage, collapse of the plasma membrane and elongation of cellular extension of the cells, occurred within 4 hours after incubation, although some recovery or partial reversal of this effects was seen in Hs294T cells. These effects are best seen in FIGS. 2 and 3.

The effects of extract on cell survival and morphology of other cell lines are illustrated in FIG. 1. As seen therein, the extract was most effective on A375 melanoma cells, LnCaP prostate cancer cells, U937 lymphoma cells and K562 leukemia cells, because the extract was able to induce cytotoxicity in more than 75% of the cells. The extract was also moderately effective on A375M melanoma cells, AAB-1 melanoma cells, MCF-7/TNFR breast cancer cells, Hey ovarian cancer cells, H522 non-small cell ling cancer cells and Molt-4 leukemia cells, inducing the cytotoxicity of more than 50% of these cells. FIGS. 4 and 5 depict the extent of morphological changes seen in Hey cells, H322 and H522 cells, and LnCaP prostate cancer cells seen over time.

Apoptosis also plays a role in extract-sensitive tumor cells. As shown in FIG. 6, DNA extracted from control (DMSO-treated) cells remained intact; in contrast, tumor cell lines treated with the extract showed loss of DNA integrity and laddering. DNA laddering was most evident in A375 and LnCaP cells, and was discernible in non-small cell lung H322 and H522 cells.

Based on studies of plant extract by thin-layer chromatography (TLC) and detection of the resolved species, an estimated 20–50 distinct molecular species are present in this crude extract.

EXAMPLE 3

Preparation of Purified and Partially-Purified Extract (the LP9 Compound)

Two hundred male and female EO plants were used, weighing between 50 to 80 g. The plants were washed in cold water, peeled, and had their roots and latex material removed. The plants were cut into halves or quarters and blended for 2 minutes in a Waring blender with 300 ml of Chl:MeOH (1:2). The homogenate was filtered through a fritted glass funnel under vacuum. The liquid was retained and reblended with 300 ml Chl:MeOH and 80 ml of distilled water for a total volume of 380 ml. The liquid fractions were combined and placed in a large separatory funnel (680 ml total volume). The funnel was inverted 3 to 4 times and the green organic layer was removed and retained (the top white layer was discarded). The organic layer was centrifuged at 500×g for 10 min and the liquid carefully removed and placed in a Rotovap vacuum concentrator. Five hundred ml aliquots were Rotovap concentrated (bath temp 40° C.) to almost complete dryness and resuspended in 5 ml MeOH. The concentrate was removed, flask rinsed with an additional 5–10 ml MeOH and pooled with the initial concentrate. This fraction was stored at 4° C. A white precipitate forms when stored at this temperature. This precipitate has no activity and is removed by centrifugation (12,000×g, 10 min at 4° C.).

All procedures were performed at 4° C. This procedure was repeated until all plants were processed through this stage. The total volume was 300–500 ml of concentrate. Aliquots from each purification step were retained and analyzed for bioactivity by the assay described below.

To begin the purification process, a pre-cycled silica resin column (2.5×30 cm) was equipped with a solid displacement pump and equilibrated in chloroform. Concentrated extract (in 30 ml MeOH) was diluted 10-fold in Chl and applied to the silica column at a rate of 10 ml/min and 15 ml fractions were collected. The column was washed with 4 column volumes of chloroform, which removed most of the green pigmentation, and bioactivity was eluted with 5% step-increases in Chl:MeOH, starting at 95% Chl:5% MeOH. Bioactivity was completely eluted at 90% Chl:10% MeOH. These fractions were collected, pooled and concentrated by Rotovap as described above.

As the next part of the purification process, pooled activity from silica chromatography was diluted 10-fold into Chl and mixed with enough DEAE-Sephacel in Chl to partially fill a Buchner funnel (13.5×5 cm). The funnel was fitted with Whatman filter paper and DEAE-Sephacel was initially prepared in MeOH and equilibrated in Chl before mixing it with plant extract. The slurry was gently stirred for 15 min at room temperature and slowly poured into the funnel with gentle suction. The packed material was washed with 2 L of Chl and eluate was collected. The packed funnel was sequentially washed with 100% Chl, 90% Chl:10% MeOH, 80% Chl:20% MeOH and 70% Chl:30% MeOH. Collected fractions were analyzed for bioactivity (as described below) and a broad range of activity was detected. The most active fractions eluted at 70% Chl:30% MeOH. These fractions were pooled, concentrated and stored at 4° C.

The next part of the purification process involved resolving active fractions from the DEAE-Sephacel fractionation by reverse phase HPLC (Waters) on a Vydac $C_{18}$ column (1×25 cm). The column was equilibrated in double-distilled water at a flow rate of 1.5 ml/min and 1.5 ml fractions were collected throughout the run. Ten-twenty mg aliquots of partially-purified plant material were injected (in MeOH) and washed with water for 10 min. A linear gradient of increasing MeOH was applied (2%/min; 50 min) and 100% MeOH was continued for an additional 10 min. Fractions were monitored for OD at 230 nm and bioactivity. Bioactivity was detected in fractions collected at a solvent gradient of 95% MeOH:5% water. These fractions were pooled, concentrated to <1 ml and stored at 4° C.

Finally, the HPLC purified plant extract was applied to a 20×20×0.2 cm preparative silica gel plate (EM Separations, Gibbstown, N.J.) by being streaked across the bottom 2 cm portion of the plate. The plate was placed in a chromatography tank containing ethyl acetate and developed till the solvent front reached the top of the plate. The left 2 cm portion of the silica plate was segmented into 0.5 cm segments and the silica was scraped into tubes containing 100% MeOH. These 40 fractions were centrifuged to tightly pellet the silica and the methanolic supernatant was concentrated by SpeedVac and tested for bioactivity. Bioactivity was detected in samples taken at an Rf value of ~0.75 to 0.80. This region was removed by scraping with a razor blade and activity was extracted as described above. These samples were concentrated by Speed Vac and reapplied to a similar TLC plate but developed in a solvent consisting of 95% Chl:5% MeOH containing 0.25% aqueous ammonia. Bioactivity was monitored and isolated as described below. Bioactivity in this solvent system was detected at an Rf value of 0.5 to 0.6.

To analyze the purity of the extracted product, aliquots of purified plant product were spotted onto a thin-layer (0.5 mm) chromatography plate and developed in Chl:MeOH:aqueous ammonia (95:5:0.28). The homogeneity of the resolved product was initially evaluated by long and short wave UV exposure. Purified product could be detected by spraying with 3% formaldehyde, 97% sulfuric acid and charring on a hotplate. The purified product (through preparative TLC) could be detected as a single spot (Rf~0.5) by shortwave UV exposure or charring after formaldehyde:sulfuric acid spray (see FIG. 7). Bioactivity of the purified product could be detected to 1 ng/ml. The purified product was referred to as LP9. Approximately 40 mg of this purified material was available for animal studies and molecular characterization. The purified material was analyzed by UV and visible spectroscopy and electrospray mass spectroscopy. The purified product weakly absorbed light at 230 and 320 nm and was unable to be characterized by mass spectroscopy. The material was difficult to detect by HLPC resolution with UV monitor or light-scattering. The purified material was soluble in water and organic solvents, but the limits of solubility were not determined.

Figure 7:
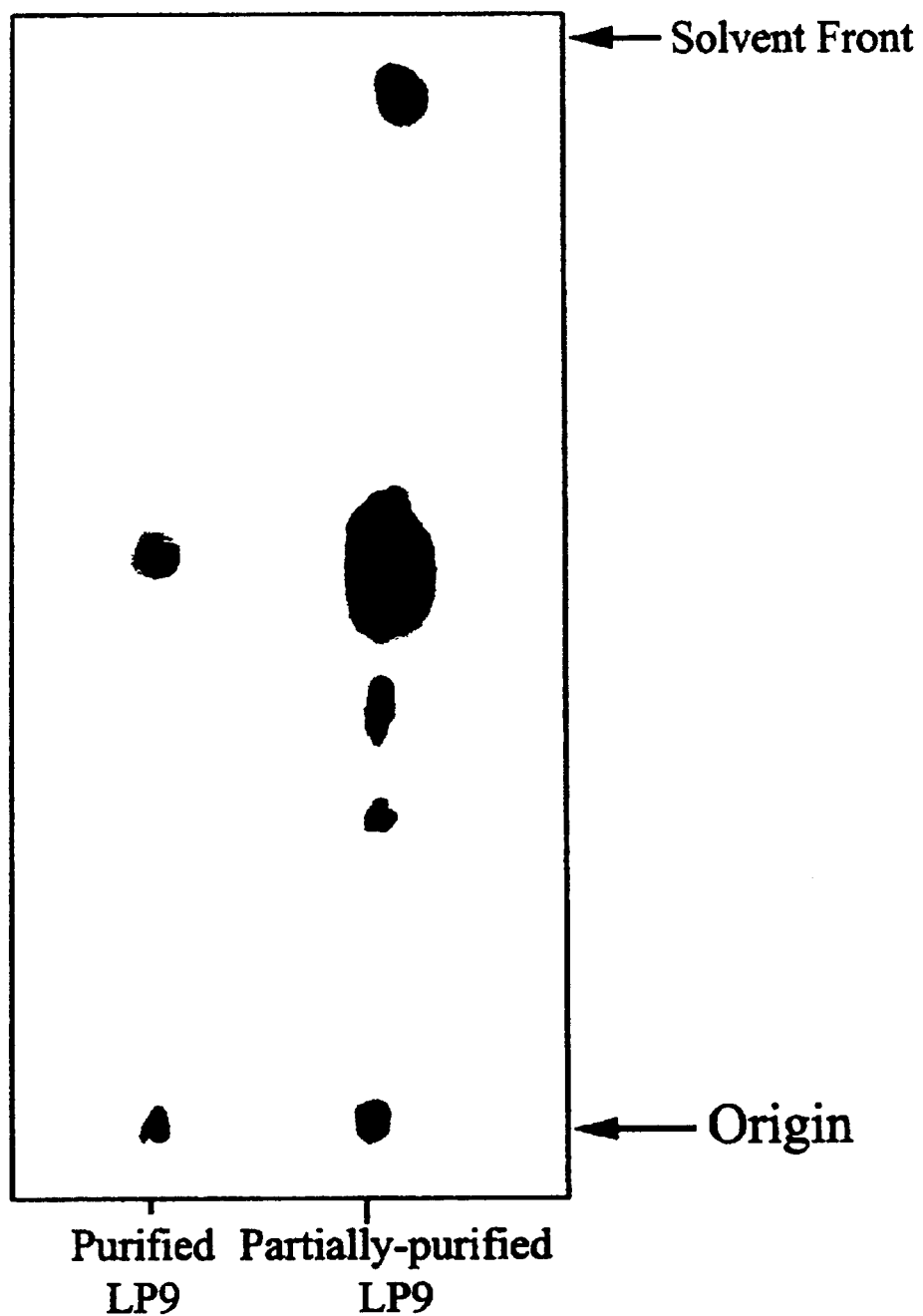
FIG. 7 comprises a scanned copy of a thin-layer chromatography plate and shows the results of thin-layer chromatography of the purified extract and partially-purified extract. Purified extract was detected as a single spot, whereas additional species are evident in the partially-purified extract.

A partially-purified extract, obtained after DEAE-Sephacel chromatography, had 6–7 detectable spots when analyzed in parallel (see FIG. 7). This material had greater 320 nm absorbance and yellow color, suggesting the yellow substance represented a contaminant in the preparation. Although not shown, fractions taken from earlier stages of purification had a greater number of colorimetric (mostly green and yellow) compounds. Due to the ease of preparation of partially-purified compound and similar bioactivity, the DEAE-Sephacel fraction was utilized in nude mouse studies with animals bearing LnCaP prostate cancer cell xenografts.

To analyze the bioactivity of the extract throughout the parts of the purification process, as well as thereafter, aliquots of plant extract (in Chl or MeOH) were Speed Vac concentrated to near dryness and washed in 1 ml MeOH. The samples were vacuum concentrated to dryness and the pellet (visible or not) was resuspended with 10 µl DMSO and diluted with 0.5 ml cell growth media (RPMI) containing 10% fetal bovine serum. This mixture was added to LnCaP prostate cancer cells growing in individual wells of a 96-well plate. LnCaP cells ($5$–$10 \times 10^3$ cells/well) were preplated in 0.1 ml RPMI media with 10% fetal bovine serum 24 hours prior to the addition of plant extract. One hundred µl of DMSO-complete media resuspended plant extract or fraction was added to wells (in duplicate). The effect of a final 1% DMSO concentration on LnCaP cell growth and survival was negligible and was monitored by incubation of LnCaP cells with 1% DMSO as a control in each bioassay. Cellular response with active compound was detected microscopically within 2 to 6 hours of plant extract or purified product incubation, with an apparent increased flattening and cellular adhesion predominating early after extract incubation. After 24 hours clustered cells become apoptotic, detected by changes in PARP cleavage, caspase activation and quantified by MTT or crystal violet assays. Due to the rapidly detectable and quantitative cellular response provided by LnCaP cells, this cell line was used for determination of bioactivity during extract purification.

Bioactivity of the extract on melanoma B cells was also evaluated by the effect of LP9 on melanin production in B16 control and treated cells in vitro. Melanin in B16 cells can be visually detected as cells approach confluence. To quantify the effects of LP9 on melanin production, 4000 cells in individual wells of a 96-well plate were treated with various dilutions of LP9 for 72 hours before cells were rinsed in PBS and lysed with lysis buffer consisting of 0.1 NaOH, 1% SDS. Cells were incubated overnight at room temperature and mixed by orbital shaker for 15 min before absorbance was read at 405 nm in a 96-well plate reader. The absorbance values are used as an estimate of relative melanin production and is reported as a percentage of absorbance measured in untreated B16 cells. These studies were conducted in conjunction with assays used to determine changes in proliferation and survival (MTT assay, crystal violet staining).

EXAMPLE 4

Effect of Purified and Partially-Purified Extract on Cell Lines

A. In Vitro Studies

As described above, EO extract was incubated with human LnCaP prostate cancer cells and murine B16 melanoma cells to determine bioactivity. Biological activity of the purified and partially-purified compound on human prostate cancer LnCaP and murine melanoma B16 cells detected distinctions in anti-tumor responsiveness in vitro. As shown in FIG. 8a, LP9 induced apoptosis and inhibited the growth of LnCaP but not B16 cells. PARP cleavage, caspase activity and growth inhibition were increased in LnCaP cells by LP9 (to 1 ng/ml), but not B16 cells. Conversely, melanin production was dose-dependently decreased by LP9 in B16 melanoma cells, as seen in FIG. 8b. Therefore, LP9 has diverse biological effects on human and murine tumor cells.

B. In Vivo Studies

1. In Vivo Toxicity:

BDF-1 male mice (18–24 g; Charles River Laboratories) were injected with LP9 intraperitoneally (i.p.) at various dose levels to determine the maximally tolerated single dose. LP9 was vacuum concentrated to near dryness and resuspended in DMSO at a concentration of 20 mg/ml. The resuspension was further diluted with an equal volume of polyethylene glycol 300 (PEG300) so that the final product was 10 mg/ml in 50% DMSO, 50% PEG300. Two animals per group were injected with 1000, 100, 10, 1 and 0.1 µg of LP9 in a total volume of 100 µl. Control animals received 100 µl of DMSO:PEG. Animals were observed at 4 hour intervals for signs of toxicity. After 4, 8 and 24 hours, all animals survived. There was a transient decrease (recovered by 8 hours) in the physical activity of animals receiving the highest dose of drug. Lethal dose of LP9 is >1 mg/18–24 g mouse or >56 mg/kg.

2. Effect of LP9 on B16 Murine Melanoma Tumor Growth in BDF-1 mice

Thirty BDF-1 male mice were anesthetized and the hair on the back of the neck was removed. B16 melanoma cells (0.1 ml of a $5 \times 10^6$ cell suspension) were injected subcutaneously into the back of the neck of all thirty mice. One day later, animals were split into 3 groups of 10 animals each. In group 1, 0.5 mg of LP9 was injected at the tumor site and an additional 0.5 mg was injected i.p. Group 2 animals received 0.5 mg at the tumor site and an additional 0.5 mg was injected intravenously (tail vein). Group 3 animals were controls and received 50 µl DMSO:PEG300 at the tumor site and 50 µl i.p. Animals receiving i.v. injections of drug were moribund and 2 of the 10 in this treatment group died after 24 hours. On day 7, to maximize drug effects without toxicity, the animals previously receiving i.v. injections (Group 2) were given i.p. injections of 1 mg, while the group 1 animals received 0.5 mg of drug through i.p. administration. Due to limited drug supply, one of the group 1 mice was sacrificed at this interval. Animals received a similar drug regimen on day 14 and were evaluated for the presence of tumor on day 20.

3. Effect of Partially-Purified LP9 on LnCaP Tumor Growth in Nude Mice

LnCaP cells were harvested from T75 flasks by trypsinization and pelleted by centrifugation. The cells were washed in PBS and held on ice. Cells were mixed with Matrigel (on ice) at a concentration of $12.5 \times 10^6$ cells/ml Matrigel and 0.1 ml aliquots were injected subcutaneously into the right dorsal quadrant of 30 male nude mice (8 weeks old, ~22 g). After 9 days, small tumors with angiogenic boundaries were present in 20 of 30 animals. These animals were randomly separated (on day 10) into 2 equal groups with one group receiving a single i.p. injection of 300 µg partially-purified LP9 (through DEAE-Sephacel purification) in 100 µl DMSO:PEG300 (1:1). The other group received 100 µl DMSO:PEG300 as a control. Tumor volumes were recorded every 2–3 days (with calipers) and total tumor burden was averaged for each group. All animals were sacrificed 28 days after initial inoculation.

Thus, the in vivo studies were conducted with 2 distinct tumor models and 2 distinct extract preparations. The initial studies were conducted on BDF-1 mice bearing subcutaneous tumors. Animals were inoculated with B16 melanoma cells and treated three times with purified LP9 by two routes of administration. As shown in FIG. 9, animals in both treatment groups were injected at the site of tumor inoculation. The remaining dose was injected intraperitoneally (group 1) or intravenously (group 2) and distinct responses were noted. In the control group, 9 of 10 animals had easily detectable tumor burden (>1.5 cm diameter). The group receiving tumor site injections combined with i.v. injections had no evidence of an anti-tumor effect in 7 of 8 animals (87.5%). However, only 3 of 9 animals receiving LP9 through tumor injection site delivery and i.p. injections had measurable tumor. Together with in vitro studies, these results suggest a mechanism of LP9 anti-tumor activity that was dependent on the route of administration.

Figure 10:
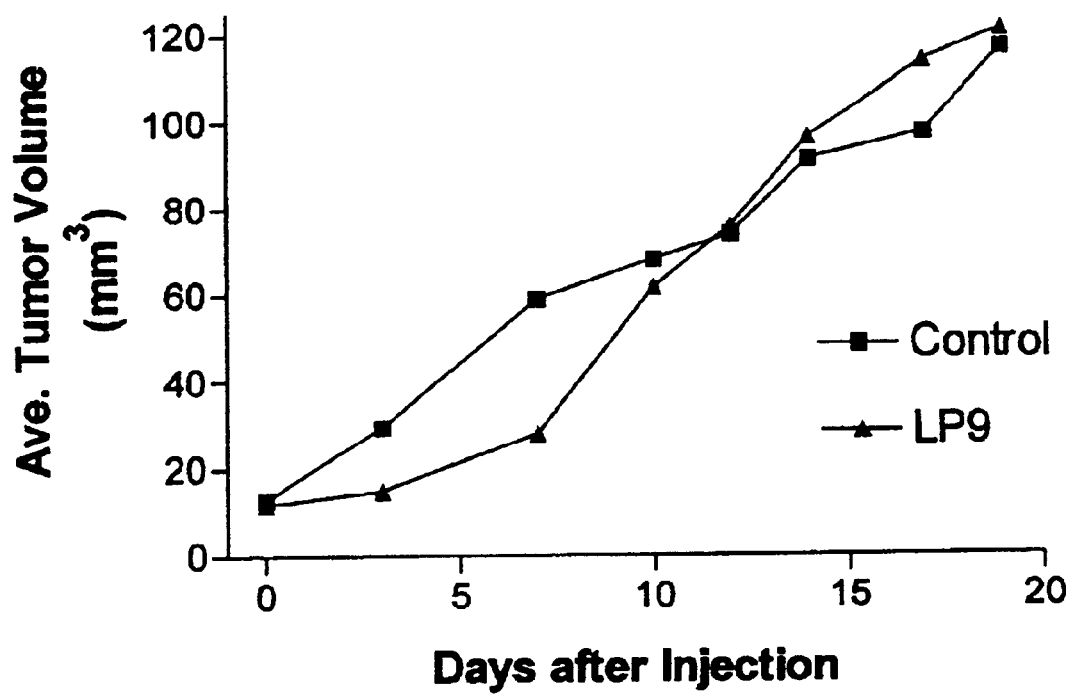
FIG. 10 is a chart showing the effect of partially-purified extract on LnCaP tumor xenografts in nude mice. LnCaP cells were injected subcutaneously into nude mice and tumors were visible after 9 days. Animals received partially-purified extract injections or control injections, starting on the first day. Tumor volumes were measured by calipers in individual mice and are plotted as total tumor burden in the population (15 animals/group). Partially-purified extract had early tumor suppressive effects up to the $9^{th}$ day after injection, but minimal overall effects on tumor growth by day 19.

The direct apoptotic actions of LP9 (and partially-purified LP9) prompted and examination of in vivo anti-tumor on LnCaP xenograft tumors in nude mice. Tumors were injected and allowed to establish (10 days) before initiating therapy. Partially-purified LP9 (through DEAE-Sephacel) representing bio-activity equal to that of purified extract was used in these studies. In addition, due to limited availability and unknown toxicity in nude mice, one-third the amount of material (by weight) was injected into nude mice bearing LnCaP tumors. Animals received i.p. injections only and, as shown in FIG. 10, tumor growth was suppressed when compared to control mice. However, the effects were short-lived and no distinction in tumor burden was detected between control and treated mice 9 days after initial LP9 injection (Day 19). These results suggest possible early onset of anti-tumor effects in LnCaP tumors. However, the results were distinct when compared to B16 melanoma studies in immune-competent animals, raising the possibility that host anti-tumor effects may contribute to the activity of LP9. Other parameters that may also be affect the in vivo anti-tumor response including the route of drug delivery and the purity of the extract.

While preferred method embodiments have been shown and described, it will be apparent to one of ordinary skill in the art that numerous alterations may be made without departing from the spirit or scope of the invention. The invention is not to be limited except in accordance with the following claims and their legal equivalents.

What we claim is:

1. A process of isolating purified fraction from a *Euphorbia obesa* plant, comprising:
   preparing a sample of said plant by:
      rinsing said plant with water,
      removing and discarding root, outer cortex, and latex material of the plant,
      thereby forming the sample from the remaining material of the plant comprised substantially of a bulb portion of the plant;
   dissolving said sample with a first solvent comprising methanol and chloroform to form a solution;
   separating said solution into an aqueous upper layer and an aqueous pulp-like lower layer;
   isolating the aqueous pulp-like lower layer from the aqueous upper layer;
   exchanging the first solvent for a second solvent comprising a solvent chosen from the group consisting of dimethylsulfoxide, methanol, or hexane:chloroform; and
   purifying said pulp fraction to produce a purified fraction which induces apoptosis and inhibits growth of a cancerous cell.

2. The process of claim 1 wherein said plant weighs less than 100 g.

3. The process of claim 1 wherein said process further comprises exchanging said first solvent of said pulp fraction with a second solvent.

4. The process of claim 3 wherein said step of solvent exchange comprises evaporating said pulp fraction into a concentrate and dissolving said concentrate into a second solvent.

5. The process of claim 3 wherein said second solvent is selected from the group consisting of DMSO, methanol and a combination of hexane and chloroform.

6. The process of claim 1 wherein said purifying step comprises eluting said pulp fraction through a silica gel column with 90% chlorine and 10% methanol.

7. The process of claim 1 wherein said purifying step comprises eluting said pulp fraction through a silica gel column with 80% hexane and 20% ethyl acetate.

8. The process of claim 1 wherein said purifying step comprises eluting said pulp fraction through a silica gel column with 70% hexane and 30% ethyl acetate.

9. The process of claim 1 wherein said purifying step further comprises sequentially eluting said pulp fraction with DEAE-Sephacel in chlorine with 70% chlorine and 30% methanol.

10. The process of claim 1 wherein said purifying step further comprises resolving said pulp fraction by reverse phase HPLC with 95% methanol and 5% water.

11. The process of claim 1 further comprising detecting the bioactivity of said pulp fraction by incubating said fraction with an amount of LnCaP prostate cancer cells and determining apoptosis in 50% or greater of said cells.

12. The process of claim 1 wherein said cancerous cell is a mammalian cell.

13. The process of claim 12 wherein said cancerous cell is a human cell.

14. The process of claim 1 wherein said cancerous cell is a melanoma cell.

15. The process of claim 14 wherein said melanoma cell is selected from the group consisting of a Hs294T, A375P, A375M, M-21, AAB-1, AAB-2 and B-16 cell.

16. The process of claim 14 wherein said melanoma cell is a B-16 cell.

17. The process of claim 1 wherein said cancerous cell is a non-small cell lung cancer cell.

18. The process of claim 17 wherein said non-small cell lung cancer cell is selected from the group consisting of a H322 and H522 cell.

19. The process of claim 1 wherein said cancerous cell is a prostate cancer cell.

20. The process of claim 19 wherein said prostate cancer cell is selected from the group consisting of a LnCaP and PC-3 cell.

21. The process of claim 19 wherein said prostate cancer cell is a LnCaP cell.

22. The process of claim 1 wherein said cancerous cell is a breast carcinoma cell.

23. The process of claim 22 wherein said breast carcinoma cell is selected from the group consisting of a MCF-7, MCF-7/TNFR and SKBr-3 cell.

24. The process of claim 1 wherein said cancerous cell is an ovarian cancer cell.

25. The process of claim 24 wherein said ovarian cancer cell is a Hey cell.

26. The process of claim 1 wherein said cancerous cell is a lymphoma cell.

27. The process of claim 26 wherein said lymphoma cell is selected from the group consisting of a Jurkat and U937 cell.

28. The process of claim 1 wherein said cancerous cell is a leukemia cell.

29. The process of claim 28 wherein said leukemia cell is selected from the group consisting of a K562, MOLT-4 and THP-9 cell.

30. A method for inducing apoptosis and growth inhibition of a cancerous cell comprising
   isolating an extract of *Euphorbia obesa* according to the steps of claim 1; and
   contacting said cancerous cell with effective amount of said extract.

31. The method of claim 30 wherein said extract is derived from the bulb portion of the plant.

32. The method of claim 30 wherein said extract comprises a single compound.

33. The method of claim 30 wherein said extract comprises a plurality of compounds.

34. The method of claim 30 wherein said cancerous cell is contacted by said extract in vitro.

35. The method of claim 30 wherein said cancerous cell is contacted by said extract in vivo.

36. The method of claim 35 wherein said effective amount is administered directly to a tumor site.

37. The method of claim 36 wherein said effective amount is further administered intra-peritonially.

38. The method of claim 30 wherein said efifective amount is at least 0.5 mg.

39. The method of claim 31 wherein said cancerous cell is a mammalian cell.

40. The method of claim 39 wherein said cancerous cell is a human cell.

41. The method of claim 31 wherein said cancerous cell is a melanoma cell.

42. The method of claim 41 wherein said melanoma cell is selected from the group consisting of a Hs294T, A375P, A375M, M-21, AAB-1, AAB-2 and B-16 cell.

43. The method of claim 43 wherein said melanoma cell is a B-16 cell.

44. The method of claim 31 wherein said cancerous cell is a non-small cell lung cancer cell.

45. The method of claim 44 wherein said non-small cell lung cancer cell is selected from the group consisting of a H322 and H522 cell.

46. The method of claim 31 wherein said cancerous cell is a prostate cancer cell.

47. The method of claim 46 wherein said prostate cancer cell is selected from the group consisting of a LnGaP and PC-3 cell.

48. The method of claim 46 wherein said prostate cancer cell is a LnCaP cell.

49. The method of claim 31 wherein said cancerous cell is a breast carcinoma cell.

50. The method of claim 49 wherein said breast carcinoma cell is selected from the group consisting of a MCF-7, MCF-7/TNFR and SKBr-3 cell.

51. The method of claim 31 wherein said cancerous cell is an ovarian cancer cell.

52. The method of claim 51 wherein said ovarian cancer cell is a Hey cell.

53. The method of claim 31 wherein said cancerous cell is a lymphoma cell.

54. The method of claim 53 wherein said lymphoma cell is selected from a group consisting of a Jurkat and U937 cell.

55. The method of claim 31 wherein said cancerous cell is a leukemia cell.

56. The method of claim 55 wherein said leukemia cell is selected from a group consisting of a K562, MOLT-4 and THP-9 cell.

57. A process of isolating a purified fraction from a *Euphorbia obesa* plant, comprising the steps of:
   preparing a sample of said plant by rinsing said plant with water and removing and discarding said plant's outer cortex, latex material, and roots;
   reducing said sample into a slurry;
   dissolving said slurry with a first solvent consisting essentially of chloroform and methanol to form a solution;
   separating said solution into a upper liquid layer and a lower liquid pulp fraction; and
   purifying said pulp fraction with a silica gel column eluted with a solvent system chosen from the group consisting of 90% chlorine and 10% methanol, 80% hexane and 20% ethyl acetate, and 70% hexane and 30% ethyl acetate to produce a purified fraction which induces apoptosis and inhibits growth of a cancerous cell.

* * * * *